(12) United States Patent
Nagae et al.

(10) Patent No.: US 10,182,773 B2
(45) Date of Patent: Jan. 22, 2019

(54) RADIATION FLUOROSCOPY APPARATUS

(71) Applicant: SHIMADZU CORPORATION, Nakagyo-Ku, Kyoto-Shi, Kyoto (JP)

(72) Inventors: Kodai Nagae, Kyoto (JP); Tsuyoshi Sasagawa, Kyoto (JP); Takayuki Sano, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 177 days.

(21) Appl. No.: 15/352,130

(22) Filed: Nov. 15, 2016

(65) Prior Publication Data

US 2018/0132803 A1 May 17, 2018

(51) Int. Cl.
*A61B 6/00* (2006.01)
*A61B 6/12* (2006.01)

(52) U.S. Cl.
CPC .............. *A61B 6/4014* (2013.01); *A61B 6/12* (2013.01); *A61B 6/487* (2013.01); *A61B 6/56* (2013.01)

(58) Field of Classification Search
CPC ............................... A61B 6/4014; A61B 6/487
See application file for complete search history.

(56) References Cited

U.S. PATENT DOCUMENTS 6,307,914 B1 10/2001 Kunieda et al.
2017/0036041 A1* 2/2017 Reichert ................ A61B 6/032

FOREIGN PATENT DOCUMENTS

JP 2000-167072 6/2000
JP 2014-128412 7/2014
JP 2015-057194 3/2015

OTHER PUBLICATIONS

JP 2015-105183, Notification of Reasons for Refusal dated Jun. 19, 2018, 4 pages—Japanese, 3 pages—English.

* cited by examiner

*Primary Examiner* — Dani Fox
(74) *Attorney, Agent, or Firm* — Andrew F. Young, Esq.; Lackenbach Siegel, LLP

(57) ABSTRACT

A radiation fluoroscopy apparatus provides radiation fluoroscopy from at least three positions without moving the radiation irradiation element and the radiation detector. A control element includes a detection rate calculation element that respectively calculates the detection rate of the position of the marker in a first imaging system having a first X-ray tube and a first flat panel detector, a second imaging system having a second X-ray tube and a second flat panel detector, and a third imaging system having a third X-ray tube and a third flat panel detector, and a fourth imaging system having a fourth X-ray tube and a fourth flat panel detector; and an imaging system selection element that selects the two imaging systems, used for X-ray fluoroscopy, out of one of the imaging systems based on a detection rate of a position of a marker calculated by a detection rate calculation element.

5 Claims, 5 Drawing Sheets

RADIATION FLUOROSCOPY APPARATUS

CROSS REFERENCE TO RELATED APPLICATIONS

This application relates to, but does not claim priority from, JP Ser. No. 2015-105183 filed May 25, 2016, the entire contents of which are incorporated herein by reference.

FIGURE SELECTED FOR PUBLICATION

FIG. 1

BACKGROUND OF THE INVENTION

Field of the Invention

The present invention relates to a radiation fluoroscopy apparatus, such as an X-ray fluoroscopy apparatus, that detects the position of a marker or a specific region moving along with the body movement of a subject by taking an image including an implanted marker in the body of the subject or an image of the specific region of the subject from two different directions each other.

Description of the Related Art

A radiation must be irradiated exactly to an affected region relative to a radiation therapy device, having a head that irradiates the therapeutic beam and a gantry to rotate the head around a subject as the center, that performs a radiation therapy by irradiating the therapeutic beam, including e.g., X-ray and electron beam and so forth to the affected region such as a tumor and so forth. Nevertheless, in some cases, not only the subject unintentionally may move the body thereof, but also the affected area per se may move. For example, a tumor near the lung largely moves depending on breathing. Accordingly, Patent Document 1 discloses a radiation therapeutic device comprising the system, in which the X-ray fluoroscopic device detects the position of a metal marker in place near the tumor and then the therapeutic radiation to be irradiated is controlled thereby.

As such radiation therapy device, Patent Document 2 discloses an X-ray fluoroscopy apparatus that identifies the position of the marker by fluoroscoping the image including the marker implanted inside the body of the subject. According to Patent Document 2, the X-ray fluoroscopy apparatus detects an implanted marker inside body by a template matching and so forth by using a first imaging system including a first X-ray tube that irradiate an X-ray from the floor surface side and a first X-ray detector that detects the X-ray passing through the subject and a second imaging system including a second X-ray tube that irradiate an X-ray from the floor surface side and a second X-ray detector that detects the X-ray passing through the subject. And a 3 dimensional positional data can be acquired by utilizing a 2 dimensional fluoroscopy image imaged by the first imaging system and a 2 dimensional fluoroscopy image imaged by the second imaging system. Accordingly, the maker of the region to be moved is detected with a high degree of accuracy by performing continuously such operation and calculating the 3 dimensional positional data. And an irradiation of the therapeutic radiation is controlled based on the positional data of the marker so that the irradiation of the radiation corresponding to the move of the tumor can be performed with a high degree of accuracy.

At this time, the therapeutic beam must be irradiated from various directions to the affected region corresponding to the position of the affected region of the subject and so forth, so that, as described above, the head to irradiate the therapeutic beam is rotatable around the subject as the center thereof. Accordingly, according to the X-ray fluoroscopy apparatus of Patent Document 2, the first imaging system and the second imaging system must perform the fluoroscopy from the position not blocking the X-ray with the head. To enable such operation, according to the X-ray fluoroscopy apparatus of Patent Document 2, the first X-ray tube and the first X-ray detector and the second X-ray tube and the second X-ray detector are structured to be movable along a rail, so that the X-ray fluoroscopy can be performed from three preset positions.

RELATED PRIOR ART DOCUMENTS

Patent Document

Patent Document 1: JP Patent Published 2000-167072 A1
Patent Document 2: JP Patent Published 2014-128412 A1

Aspects and Summary of the Invention

According to one aspect of the present invention, there is provided a radiation fluoroscopy apparatus provides radiation fluoroscopy from at least three positions without moving the radiation irradiation element and the radiation detector. A control element includes a detection rate calculation element that respectively calculates the detection rate of the position of the marker in a first imaging system having a first X-ray tube and a first flat panel detector, a second imaging system having a second X-ray tube and a second flat panel detector, and a third imaging system having a third X-ray tube and a third flat panel detector, and a fourth imaging system having a fourth X-ray tube and a fourth flat panel detector; and an imaging system selection element that selects the two imaging systems, used for X-ray fluoroscopy, out of one of the imaging systems based on a detection rate of a position of a marker calculated by a detection rate calculation element.

Objects to be Solved

As described above, the X-ray fluoroscopy apparatus according to Patent Document 2 is a good system in which the subject can be fluoroscoped from plural positions by using the first imaging system and the second imaging system comprising the X-ray tube and the X-ray detector respectively, but a moving mechanism is mandatory to move the X-ray tube and the X-ray detector.

The present invention is completed to solve the above problem and the first purpose of the present invention is to provide a radiation fluoroscopy apparatus by which the radiation fluoroscopy can be performed from at least three positions without moving the radiation irradiation element and the radiation detector.

Further, in such case, a degree of the detection accuracy for the marker or a specific region that moves along with the body movement of the subject depending on the position of the affected region or the direction of the subject or the moving condition of the affected region may be worsened. Accordingly, the second purpose of the present invention is to provide a radiation fluoroscopy apparatus that can improve the degree of detection accuracy relative to the marker or the specific region.

Further, when the heat accumulates and is stored more than a preset value in the radiation irradiation element due to continuous irradiations from the radiation irradiation element to perform the radiation fluoroscopy, the irradiation must be temporally suspended in order to cool down the radiation irradiation element. Accordingly, the third purpose of the present invention is to provide a radiation fluoroscopy apparatus in which the radiation irradiation element can be used efficiently.

Means for Solving the Problem

According to the first invention, the radiation fluoroscopy apparatus that detects the position of a marker or a specific region moving along with the body movement of a subject by taking an image including an implanted marker in the body of the subject or an image of the specific region of the subject from two different directions each other comprises: a radiation irradiation element; at least 3 imaging systems having a radiation detector that detects the radiation irradiated from said radiation irradiation element and transmitting said subject; and an imaging system selection element that selects 2 imaging systems, which are used for a radiation fluoroscopy, out of at least the 3 imaging systems.

According to the second invention, the radiation fluoroscopy apparatus having at least 3 imaging systems comprises: a detection rate calculation element that calculates the respective detection rates of the position of the marker or the specific region relative to at least 3 imaging systems, wherein the imaging system selection element selects 2 imaging systems based on the detection rates, calculated by the detection rate calculation element, of the position of the marker or the specific region.

According to the third invention, the radiation fluoroscopy apparatus having at least 3 imaging systems comprises heat storage amounts calculation element that calculates the respective heat storages of the radiation irradiation element, wherein the imaging system selection element selects 2 imaging systems based on the detection rates, calculated by the detection rate calculation element, of the position of the marker or the specific region.

According to the fourth invention, the radiation fluoroscopy apparatus that detects the position of a marker or a specific region moving along with the body movement of a subject by taking an image including an marker implanted inside the body of the subject or an image of the specific region of the subject from two different directions each other comprises: a radiation irradiation element; a first, a second, a third, a fourth imaging system having a radiation detector that detects the radiation irradiated from the radiation irradiation element and transmitting the subject; a first electric power supply element that supplies electric power to the radiation irradiation element of the first imaging system and the second imaging system, a second electric power supply element that supplies electric power to the radiation irradiation element of the third imaging system and the fourth imaging system, an imaging system selection element that selects either the first imaging system or the second imaging system, and either the third imaging system or the fourth imaging system, as the imaging system used for the radiation fluoroscopy.

According to the fifth invention, the radiation fluoroscopy apparatus comprises: a detection rate calculation element that calculates the respective detection rates of the position of the marker or the specific region relative to the first imaging system, the second imaging system, the third imaging system, the fourth imaging system; wherein the imaging system selection element selects an imaging system having a higher detection rate of the marker or the specific region calculated by the detection rate calculation element of either the first imaging system or the second imaging system, and also selects an imaging system having a higher detection rate of the marker or the specific region calculated by the detection rate calculation element of either the third imaging system or the fourth imaging system.

According to the sixth invention, the radiation fluoroscopy apparatus comprises a heat storage amount calculation element that calculates the respective heat storages of the radiation irradiation element relative to the first imaging system, the second imaging system, the third imaging system, the fourth imaging system, wherein the imaging system selection element selects an imaging system having a lower heat storage amount of the radiation irradiation element calculated by the heat storage amount rate calculation element of either the first imaging system or the second imaging system, and also selects an imaging system having a lower heat storage amount of the radiation irradiation element calculated by the heat storage amount rate calculation element of either the third imaging system or the fourth imaging system.

Effect of the Invention

According to the first invention, a radiation fluoroscopy apparatus by which the radiation fluoroscopy can be performed from at least three positions without moving the radiation irradiation element and the radiation detector based on the operation of the imaging system selection element that selects 2 imaging systems, being used for the radiation fluoroscopy, out of 3 imaging systems.

According to the second invention, 2 imaging systems used for the radiation fluoroscopy based on the detection rates, calculated by the detection rate calculation element, of the position of the marker or the specific region are selected, so that the degree of the detection accuracy as for the marker or the specific region can be improved.

According to the third invention, 2 imaging systems used for the radiation fluoroscopy based on the heat storage amount calculated by the heat storage amount calculation element are selected, so that the radiation irradiation element having lesser heat storage amount can be selected and the radiation irradiation element can be efficiently used.

According to the fourth invention, a radiation fluoroscopy apparatus by which the radiation fluoroscopy can be performed from the four positions without moving the radiation irradiation element and the radiation detector based on the operation of the imaging system selection element that selects either the first imaging system or the second imaging system and either the third imaging system or the fourth imaging system, being used for the radiation fluoroscopy. In addition, a pair of a first electric power supply element supplying the electric power to the radiation irradiation element in the first imaging system and the second imaging system and a second electric power supply element supplying the electric power to the radiation irradiation element in the third imaging system and the fourth imaging system can supply the electric power to the radiation irradiation element of the first imaging system, the second imaging system, the third imaging system and the fourth imaging system, so that the number of the electric power supply element can be cut to half and thereby the production cost of the apparatus can be lowered.

According to the fifth invention, an imaging system having a higher detection rate of the marker or the specific region calculated by the detection rate calculation element of either the first imaging system or the second imaging system is selected, and also an imaging system having a higher detection rate of the marker or the specific region calculated by the detection rate calculation element of either the third imaging system or the fourth imaging system is selected, so that the degree of the detection accuracy as for the marker or the specific region can be improved.

According to the sixth invention, an imaging system having a lower heat storage amount of the radiation irradiation element calculated by the heat storage amount rate calculation element of either the first imaging system or the second imaging system is selected, and also an imaging system having a lower heat storage amount of the radiation irradiation element calculated by the heat storage amount rate calculation element of either the third imaging system or the fourth imaging system is selected, so that the radiation irradiation element having lesser heat storage amount can be selected and the radiation irradiation element can be efficiently used.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 1:
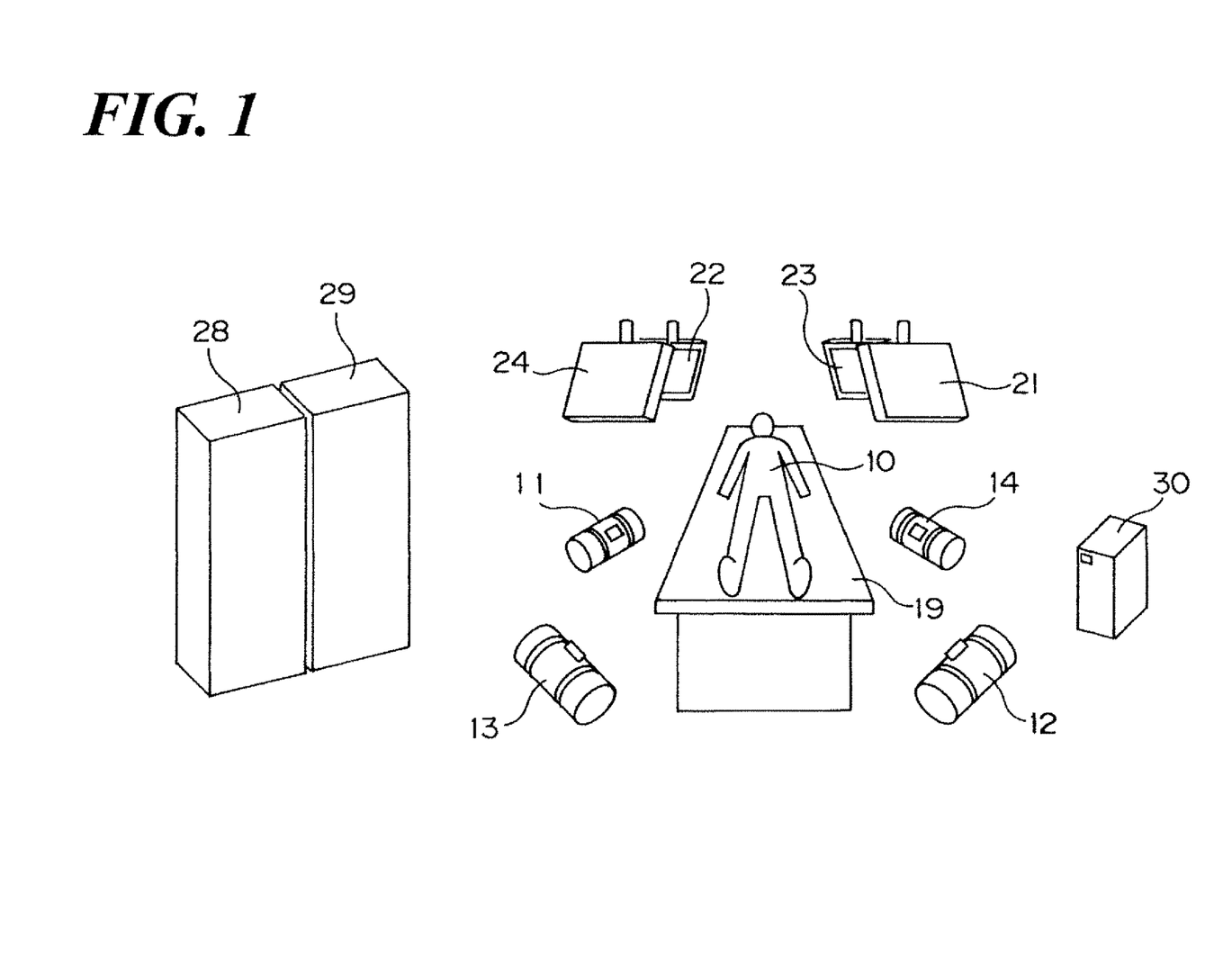
FIG. 1 is a schematic view of an X-ray fluoroscopy apparatus to be the radiation fluoroscopy apparatus according to the present invention.
Figure 2:
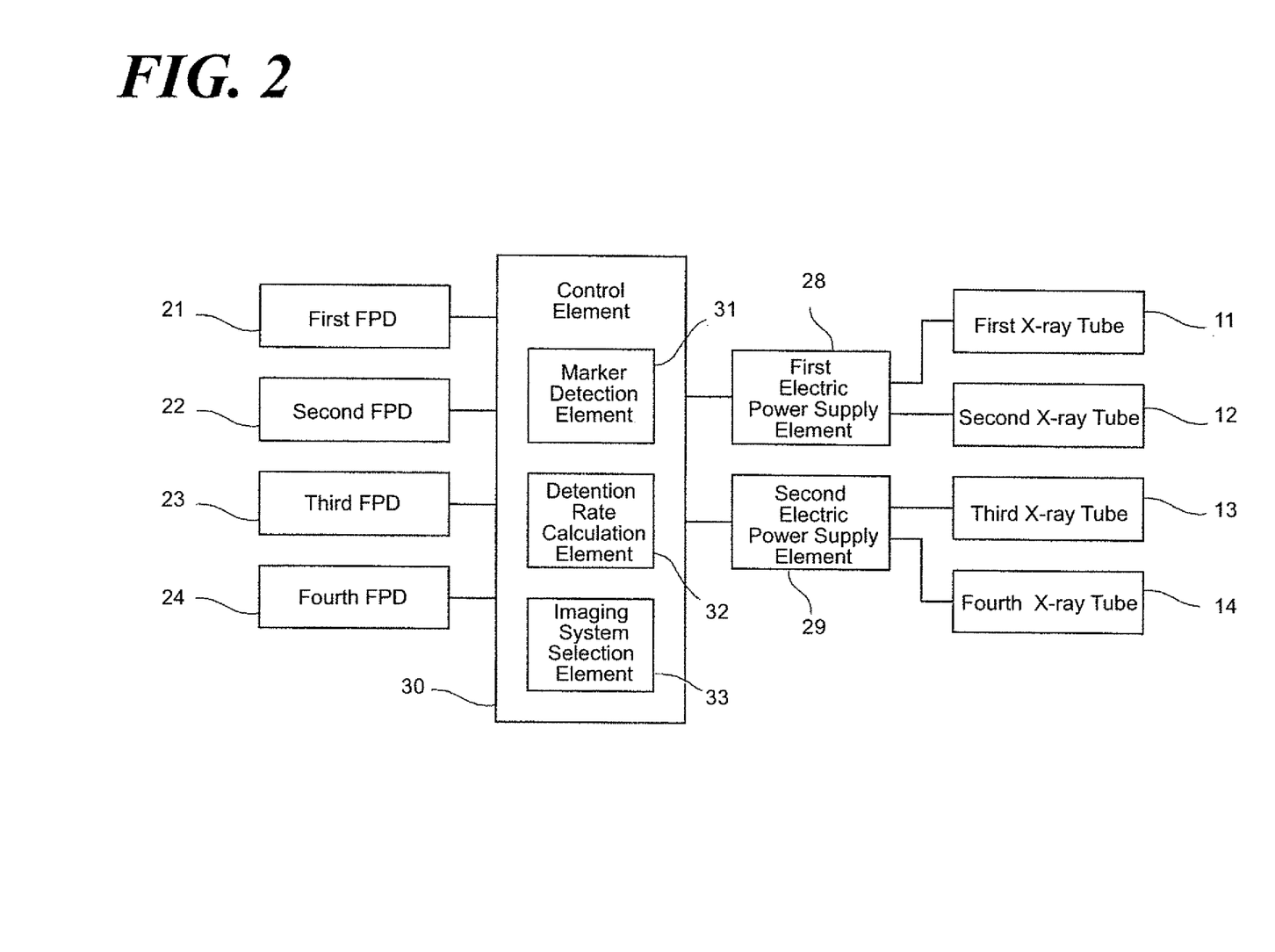
FIG. 2 is a block diagram illustrating a control system of the X-ray fluoroscopy apparatus according to the aspect of the Embodiment 1 of the present invention.

The inventors further illustrate Embodiments of the present invention following figures. FIG. 1 is a schematic view of an X-ray fluoroscopy apparatus of the radiation fluoroscopy apparatus according to the present invention. FIG. 2 is a block diagram illustrating a control system of the X-ray fluoroscopy apparatus according to the aspect of the Embodiment 1 of the present invention.

Such X-ray fluoroscopy apparatus is used together with a radiation therapy device to perform a radiation therapy by irradiating an X-ray or an electron beam to the affected region of the subject 10 on the table 19. When performing such radiation therapy, the radiation must be accurately irradiated to the affected region that moves along with the body movement of the subject 10. For such purpose, a marker is set near the affected region. And the marker implanted inside the body of the subject 10 is continuously fluoroscoped through the X-ray fluoroscopy and the two dimensional positional data as to the marker is calculated, so that the marker is detected with the high degree of accuracy, i.e., the X-ray fluoroscopy is configured to perform a dynamic tracking of the body. In addition, a marker less tracking in which a specific region such as e.g., tumor of the subject 10 is used instead of the marker may be used without setting the maker near the affected region of the subject 10.

Such X-ray fluoroscopy apparatus comprises the first X-ray tube 11, the second X-ray tube 12, the third X-ray tube 13 and the fourth X-ray tube 14, which are respectively operative as the radiation irradiation element of the present invention, and the first flat panel detector 21, the second flat panel detector 22, the third flat panel detector 23 and the fourth flat panel detector 24, which are operative as a radiation detection element of the present invention. An X-ray as radiation irradiated from the first X-ray tube 11 passes through the subject 10 on the table 19 and then after, is detected by the first flat panel detector 21. The first X-ray tube 11 and the first flat panel detector 21 constitute the first imaging system of the present invention. An X-ray as radiation irradiated from the second X-ray tube 12 passes through the subject 10 on the table 19 and then after, is detected by the second flat panel detector 22. The second X-ray tube 12 and the second flat panel detector 22 constitute the second imaging system of the present invention. An X-ray as radiation irradiated from the third X-ray tube 13 passes through the subject 10 on the table 19 and then after, is detected by the third flat panel detector 23. The third X-ray tube 13 and the third flat panel detector 23 constitute the third imaging system of the present invention. An X-ray as radiation irradiated from the fourth X-ray tube 14 passes through the subject 10 on the table 19 and then after, is detected by the fourth flat panel detector 24. The fourth X-ray tube 14 and the fourth flat panel detector 24 constitute the first imaging system of the present invention.

In addition, the X-ray fluoroscopy apparatus comprises a first electric power supply element 28 and a second electric power supply element 29. Such the first electric power supply element 28 and the second electric power supply element 29 are called a high voltage device. The first electric power supply element 28 selectively supplies a tube voltage and a tube electric current, which are required to irradiate X-rays, to the first X-ray tube 11 or the second X-ray tube 12. The second electric power supply element 29 selectively supplies a tube voltage and a tube electric current, which are required to irradiate X-rays, to the third X-ray tube 13 or the fourth X-ray tube 14.

Accordingly, the first X-ray tube 11 and the second X-ray tube 12 cannot irradiate an X-ray at the same time, and the third X-ray tube 13 and the fourth X-ray tube 14 cannot irradiate an X-ray at the same time. Therefore, as above described, the first imaging system and the second imaging system cannot be used at the same time and the third imaging system and the fourth imaging system cannot be used at the same time. On the other hand, when tracking the moving body, to calculate the two dimensional position data of the maker or the specific region (hereafter collectively called "marker"), the marker must be fluoroscoped from two different directions. Therefore, according to the present X-ray fluoroscopy apparatus, an X-ray fluoroscopy using the first imaging system and the third imaging system at the first position, an X-ray fluoroscopy using the second imaging system and the fourth imaging system at the second position, an X-ray fluoroscopy using the second imaging system and the third imaging system at the third position, and an X-ray fluoroscopy using the second imaging system and the fourth imaging system at the fourth position can be accomplished.

Further, the X-ray fluoroscopy apparatus comprises a CPU that executes the logic operation, a ROM that stores operation programs required to control the apparatus, a RAM that stores temporally the data and so forth when controlling, and so forth, and a control element 30 that controls the entire apparatus. The control element 30 is connected to the above described the first flat panel detector 21, the second flat panel detector 22, the third flat panel detector 23 and the fourth flat panel detector 24. Further, the control element 30 is also connected to, above described, the electric power supply element 28 and the second electric power supply element 29.

The control element 30 comprises a marker detection element 31 that detects the marker using two imaging systems out of the first imaging system, the second imaging system, the third imaging system, and the fourth imaging system. The marker detection element 31 calculates the two dimensional position data of the marker by a template matching comparing; an image including the marker implanted inside of the body of the subject 10 imaged with the first imaging system, the second imaging system, the third imaging system, and the fourth imaging system; and the preset template image. Further, the control element 30, as later described, comprises: a detection rate calculation element 32 that respectively calculates the detection rate of the position of the marker in the first imaging system, the second imaging system, the third imaging system, and the fourth imaging system; and an imaging system selection element 33 that selects the tow imaging systems, used for the X-ray fluoroscopy, out of the first imaging system, the second imaging system, the third imaging system, and the fourth imaging system based on the detection rate of the position of the marker calculated by the detection rate calculation element 32.

Figure 3:
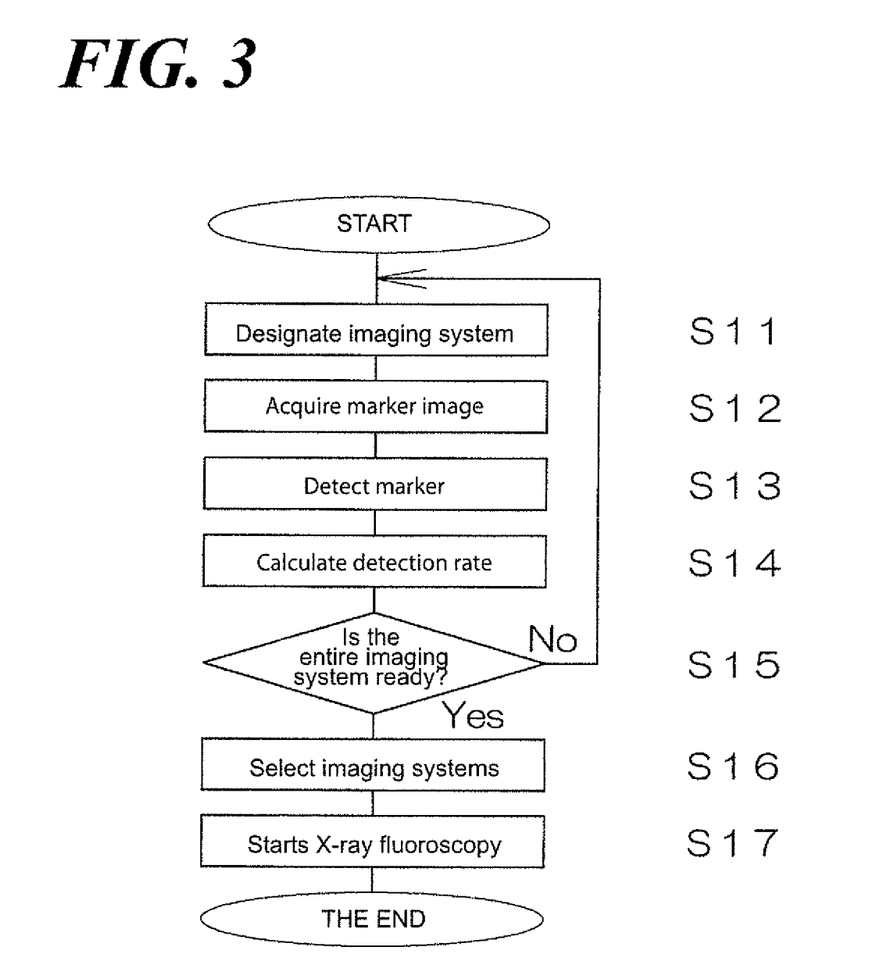
FIG. 3 is a flow-chart illustrating the operations when 1 imaging systems being used for an X-ray fluoroscopy are selected and an X-ray fluoroscopy is started according to the aspect of the Embodiment of the present invention.

Next, the inventors set forth the operations from the time when 2 imaging systems being used for the X-ray fluoroscopy are selected until the time when the X-ray fluoroscopy is started with the X-ray fluoroscopy apparatus. FIG. 3 is a flow-chart illustrating the operation by which the X-ray fluoroscopy apparatus according to the aspect of the Embodiment 1 of the present invention selects 2 imaging systems being used for an X-ray fluoroscopy until the X-ray fluoroscopy starts.

When an X-ray fluoroscopy is performed, firstly, one imaging system among the first imaging system, the second imaging system, the third imaging system, and the fourth imaging system is designated (Step S11). At this time, any imaging system of the first imaging system, the second imaging system, the third imaging system, and the fourth imaging system can be selected and designated, but also one imaging system among the imaging systems being used the X-ray fluoroscopy right before can be selected. Such selection can be executed automatically by the control element 30. Though, the operator can execute manually such selection.

Next, images including the marker implanted inside body of the subject 10 are acquired at the frame rate approximately in the range of 20 to 30 fps using the selected imaging system (Step S12). Then, referring to FIG. 2, the implanted marker inside body of the subject 10 is detected by the marker detection element 31 using a plurality of acquired images (Step S13). For example, a template matching can be utilized for detecting the marker.

Next, referring to FIG. 2, the detection rate calculation element 32 calculates a detection rate of the position of the marker when the marker is detected by using selected imaging system.

Specifically, the detection rate of the marker largely varies with the direction of the X-ray fluoroscopy, depending on the conditions including the position and direction of the subject 10 during the X-ray fluoroscopy and the shift of the maker along with breathing. For example, if the linear marker is used, the recognition of the maker by the X-ray fluoroscope of the marker from the axis direction thereof becomes hard. Further, if the marker overlaps a bone region in the direction of the X-ray fluoroscopy, the recognition of the marker is too hard unless a high dose radiation is used. Accordingly, the detection rate of the position of the marker of the first imaging system, the second imaging system, the third imaging system, and the fourth imaging system can be different each other. Therefore, the X-ray fluoroscopy apparatus according to the aspect of the Embodiment 1 adopts the structure in which the detection rate of the position of the marker is preliminarily calculated. And two imaging systems being used for the X-ray fluoroscopy are selected out of the first imaging system, the second imaging system, the third imaging system, and the fourth imaging system based on the calculated value of the detection rate.

In such detection rate calculation step, the ratio of the image, in which the marker can be detected in the marker detection step (Step S13), of a plurality of the images acquired in the marker image acquisition step (Step S12) can be set as the detection rate of the position of the marker. However, when the marker is detected by the pattern matching, the detection rate of the position of the marker can be calculated based on the matching rate of patterns. Further, the detection rate of the marker can be calculated by utilizing both the ratio of the images in which the marker can be detected and the matching rate of the patterns.

The above operation is executed on the first imaging system, the second imaging system, the third imaging system, and the fourth imaging system (Step S15). The two imaging systems being used for the X-ray fluoroscopy are selected out of the first imaging system, the second imaging system, the third imaging system, and the fourth imaging system (Step S16), if the detection rate of the position of the marker relative to all of the first imaging system, the second imaging system, the third imaging system, and the fourth imaging system can be calculated (Step S15).

When the imaging system is selected, as set forth above, the first imaging system and the second imaging system cannot be used at the same time and the third imaging system and the fourth imaging system cannot be used at the same time, so that either imaging system having the higher detection rate of the position of the marker is selected from the first imaging system or the second imaging system, and also either imaging system having the higher detection rate of the position of the marker is selected from the third imaging system or the fourth imaging system. Accordingly, any pattern from four patterns including the X-ray fluoroscopy at the first position using the first imaging system and the third imaging system, the second position using the first imaging system and the fourth imaging system, the third position using the second imaging system and the third imaging system, and the fourth position using the second imaging system and the fourth imaging system can be selected.

If the two imaging systems used for the X-ray fluoroscopy are selected, the X-ray fluoroscopy starts using such imaging systems (Step S17). At this time, the two imaging systems having the higher detection rate of the position of the marker are selected, so that the X-ray fluoroscopy can be performed with a high degree of accuracy.

Figure 4:
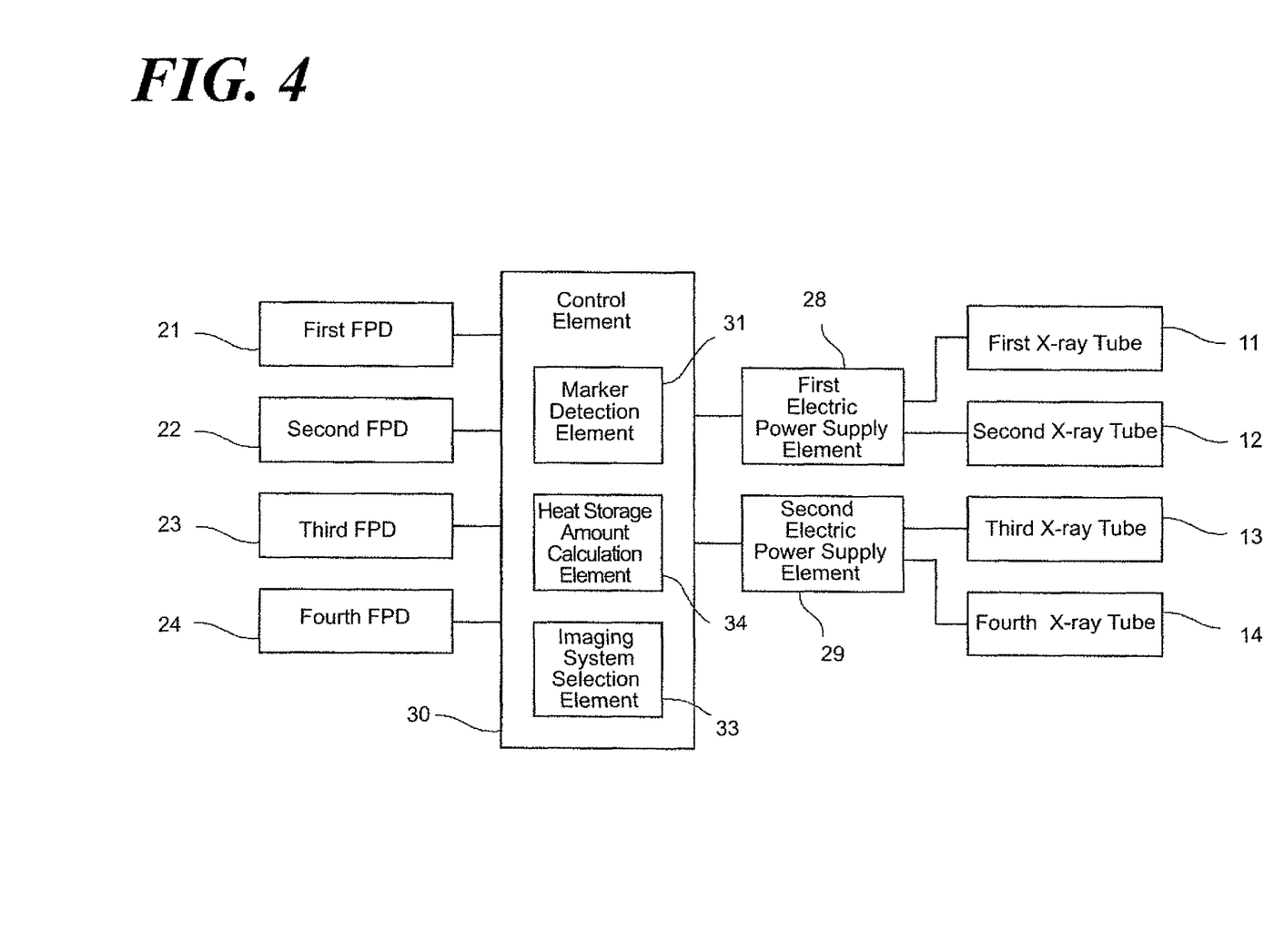
FIG. 4 is a block diagram illustrating a control system of the X-ray fluoroscopy apparatus according to the aspect of the Embodiment 2 of the present invention.

Next, the other Embodiment of the present invention, FIG. 4 is a block diagram illustrating a control system of the X-ray fluoroscopy apparatus according to the aspect of the Embodiment 2 of the present invention. Further, the same constitution as illustrated in the above described Embodiment 1 is not described in detail while providing the identical reference letter.

As set forth above, the X-ray fluoroscopy apparatus according to the aspect of the Embodiment 1 selects two imaging systems used for X-ray fluoroscopy among the first imaging system, the second imaging system, the third imaging system, and the fourth imaging system based on the detection rate of the position of the marker calculated by the detection rate calculation element 32, and the X-ray fluoroscopy apparatus according to the aspect of the Embodiment 2 selects two imaging systems used for X-ray fluoroscopy among the first imaging system, the second imaging system, the third imaging system, and the fourth imaging system based on the heat storage amount of the first X-ray tube 11, the second X-ray tube 12, the third X-ray tube 13 and the fourth X-ray tube 14 calculated by the heat storage amount calculation element 34.

Specifically, when the x-ray fluoroscopies are continuously executed, heat will be stored in the first X-ray tube, the second X-ray tube, the third X-ray tube and the fourth X-ray tube. When such stored heat is more than the specified amount, the irradiation of X-rays is suspended from safety standpoints and an X-ray irradiation from the first X-ray tube 11, the second X-ray tube, 12, the third X-ray tube 13 and the fourth X-ray tube 14 is being limited. Particularly, when the high dose X-ray is irradiate, the accumulated and stored heat per time unit in the first X-ray tube 11, the second X-ray tube 12, the third X-ray tube 13 and the fourth X-ray tube 14 can be higher than the being dissipated heat by cooling, so that the heat storage amount can be higher and an execution of the X-ray fluoroscopy can be limited. Accordingly, the X-ray fluoroscopy apparatus according to the aspect of the Embodiment 2 selects two imaging systems among the first imaging system, the second imaging system, the third imaging system, and the fourth imaging system under considering each heat storage amount in the first X-ray tube 11, the second X-ray tube 12, the third X-ray tube 13 and the fourth X-ray tube 14.

Referring to FIG. 4, the X-ray fluoroscopy apparatus according to the aspect of the Embodiment 2 comprises a heat storage amount calculation element 34 instead of the detection rate calculation element 32 of the X-ray fluoroscopy apparatus according to the aspect of the Embodiment 2. The heat storage amount calculation element 34 is structured to calculate; the heat storage amount in the first X-ray tube 11 and the second X-ray tube 12 based on the tube voltage and the tube electric current given to the first X-ray tube 11 and the second X-ray tube 12 from the first electric power supply element 28 and the X-ray irradiation time period from the first X-ray tube 11 and the second X-ray tube 12; and also to calculate the heat storage amount in the third X-ray tube 13 and the fourth X-ray tube 14 based on the tube voltage and the tube electric current given to the third X-ray tube 13 and the fourth X-ray tube 14 from the second electric power supply element 28 and the X-ray irradiation time period from the third X-ray tube 13 and the fourth X-ray tube 14.

Further, Each thermo-sensor can be attached respectively to the first X-ray tube 11, the second X-ray tube 12, the third X-ray tube 13 and the fourth X-ray tube 14; instead of calculating the heat storage amount from the tube voltage, and the tube electric current and the X-ray irradiation time; and the heat storage amount of the first X-ray tube 11, the second X-ray tube 12, the third X-ray tube 13 and the fourth X-ray tube 14 can be calculated based on the signal from the thermo-sensor.

Figure 5:
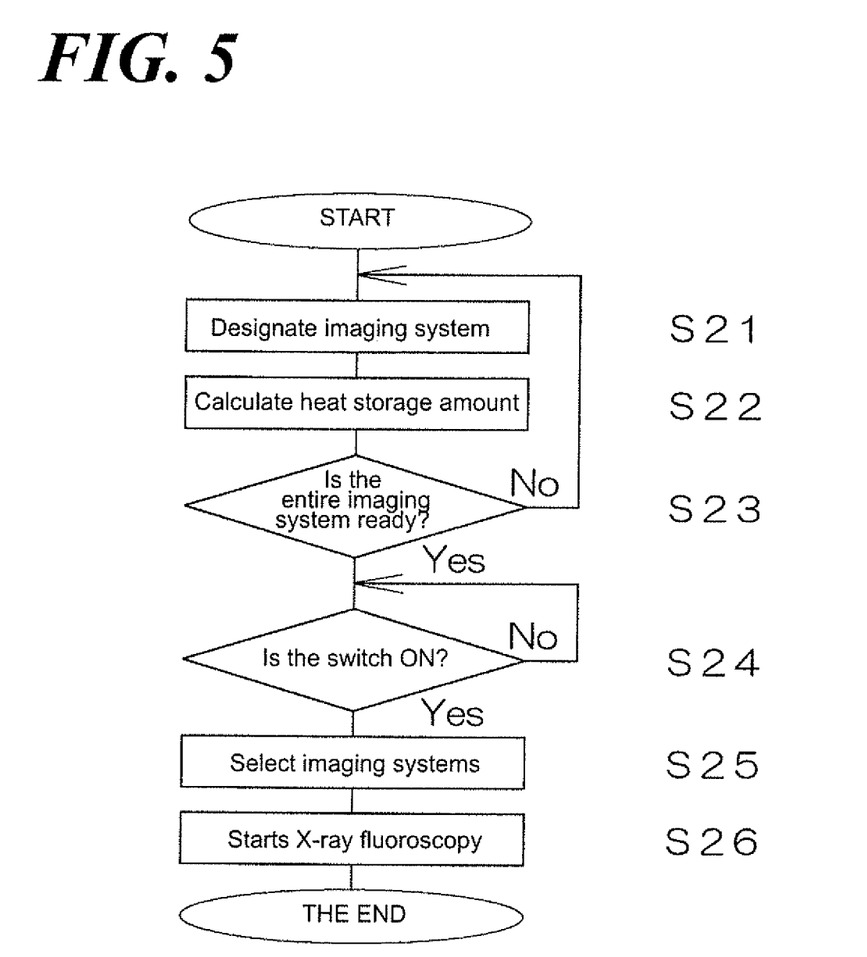
FIG. 5 is a flow-chart illustrating the operations when 2 imaging systems being used for an X-ray fluoroscopy are selected and an X-ray fluoroscopy is started according to the aspect of the Embodiment 2 of the present invention.

Next, the inventors set forth the operations when 2 imaging systems being used for an X-ray fluoroscopy are selected and when until an X-ray fluoroscopy is started according to the aspect of the Embodiment 2 of the present invention. FIG. 5 is a flow-chart illustrating the operation by which the X-ray fluoroscopy apparatus according to the aspect of the Embodiment 2 of the present invention selects 2 imaging systems being used for an X-ray fluoroscopy until the X-ray fluoroscopy starts.

When an X-ray fluoroscopy is performed, firstly, one imaging system among the first imaging system, the second imaging system, the third imaging system, and the fourth imaging system is designated (Step S21), as well as the aspect of the Embodiment 1.

Next, each heat storage amount of the first X-ray tube 11, the second X-ray tube 12, the third X-ray tube 13 and the fourth X-ray tube 14 (Step S22) is calculated. The above operation is executed on the first imaging system, the second imaging system, the third imaging system, and the fourth imaging system (Step S23). When all heat storage amounts of the first X-ray tube, the second X-ray tube 12, the third X-ray tube 13 and the fourth X-ray tube 14 relative to the first imaging system, the second imaging system, the third imaging system, and the fourth imaging system (Step S23), it is hold that the switch, not shown in FIG., is pushed down to start the X-ray fluoroscopy (Step S24).

The two imaging systems being used for the X-ray fluoroscopy are selected out of the first imaging system, the second imaging system, the third imaging system, and the fourth imaging system (Step S25) when the switch is pushed down to start the X-ray fluoroscopy (Step S24)

When the imaging system is selected, as set forth above, the first imaging system and the second imaging system cannot be used at the same time and the third imaging system and the fourth imaging system cannot be used at the same time, so that either imaging system having the lesser heat storage amount is selected from the first imaging system or the second imaging system, and also either imaging system having the lesser heat storage amount is selected from the third imaging system or the fourth imaging system. Specifically, the heat storage amounts of the first X-ray tube 11 and the second X-ray tube 12 are compared and if the heat storage amount of the first X-ray tube 11 is lesser, the first imaging system is selected and if the heat storage amount of the second X-ray tube 12 is lesser, the second imaging system is selected. As well, the heat storage amounts of the third X-ray tube 13 and the fourth X-ray tube 14 are compared and if the heat storage amount of the third X-ray tube 13 is lesser, the third imaging system is selected and if the heat storage amount of the fourth X-ray tube 14 is lesser, the fourth imaging system is selected. Accordingly, any pattern from four patters including the X-ray fluoroscopy at the first position using the first imaging system and the third imaging system, the second position using the first imaging system and the fourth imaging system, the third position using the second imaging system and the third imaging system, and the fourth position using the second imaging system and the fourth imaging system can be selected.

After the selection step to select two imaging systems used for the X-ray fluoroscopy is completed, the X-ray fluoroscopy starts using such imaging systems (Step S26). At this time, two imaging systems having the X-ray tube storing lesser heat storage amount are selected, so that the time to cool down the X-ray tube is not required and the X-ray tube can be used more efficiently.

Further, according to the aspect of the above Embodiment, the X-ray fluoroscopy comprises four imaging systems of the first imaging system comprising the first X-ray tube 11 and the first flat panel detector 21, the second imaging system comprising the second X-ray tube 12 and the second flat panel detector 22, the third imaging system comprising the third X-ray tube 13 and the third flat panel detector 23, the fourth imaging system comprising the fourth X-ray tube 14 and the fourth flat panel detector 24, but the X-ray fluoroscopy apparatus comprising at least three imaging systems thereof can be operative. Specifically, if the structure comprises; at least three imaging systems having the X-ray tube and the flat panel detector; and two imaging systems being used for the X-ray fluoroscopy can be selected from at least three imaging systems; it can be operative.

Further, according to the aspect of the Embodiment above described, the structure that can selectively supply the necessary tube voltage and the necessary tube electric current to the first X-ray tube 11 or the second X-ray tube 12 in order to irradiate an X-ray by the first electric power supply element 28; and selectively supply the necessary tube voltage and the necessary tube electric current to the third X-ray tube 13 or the fourth X-ray tube 14 in order to irradiate an X-ray by the second electric power supply element 29; is adopted. Such structure is adopted, so that the number of the electric power supply element can be cut to half and a manufacturing cost of the apparatus can be lowered. However, each electric power supply element can be respectively installed to the first X-ray tube 11, the second X-ray tube 12, the third X-ray tube 13 and the fourth X-ray tube 14. If such configuration is adopted, any two imaging systems can be selected out of the first imaging system, the second imaging system, the third imaging system, and the fourth imaging system in order to be able to perform the X-ray fluoroscopy.

In addition, according to the aspect of the Embodiment described above, the imaging system is selected based on either the detection rate of the position of the marker or the heat storage amount, but the imaging system can be selected based on both. In addition, an imaging system is unavailable due to e.g., trouble and so forth, the imaging systems excluding the troubled imaging system can be selected for the X-ray fluoroscopy.

Further, according to the aspect of the Embodiment described above, a flat panel detector as the X-ray detector operable as a radiation detector according to the present invention is applied, but an X-ray detector such as e.g., an imaging intensifier (I. I.) and other radiation detectors can be applied.

REFERENCE OF SIGN

10 Subject
11 First X-ray tube
12 Second X-ray tube
13 Third X-ray tube
14 Fourth X-ray tube
19 Table
21 First flat panel detector
22 Second flat panel detector
23 Third flat panel detector
24 Fourth flat panel detector
28 First electric power supply element
29 Second electric power supply element
30 Control element
31 Marker detection element
32 Detection rate calculation element
33 Imaging system selection element
34 Heat storage amount calculation element Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:
1. A radiation fluoroscopy apparatus, that detects a position of at least one of an implanted marker and a specific region moving along with a body movement of a subject by taking an image including said implanted marker inside one of said body of said subject and an image of said specific region of said subject from two different directions, the radiation fluoroscopy apparatus comprises:
   a radiation irradiation element;
   at least three different imaging systems each having a radiation detector that detects a radiation irradiated from said radiation irradiation element and transmitting said subject;
   an imaging system selection element that selects at least two of said at least three imaging systems, being used for a radiation fluoroscopy;
   a detection rate calculation circuit calculates a respective detection rate of at least one of a position of said implanted marker and said specific region relative to each of said least three imaging systems; and
   said imaging system selection element selects at least two of said imaging systems based upon each said detection rates, calculated by said detection rate calculation element, of one of said position of said implanted marker and said specific region.

2. A radiation fluoroscopy apparatus, that detects a position of at least one of an implanted marker and a specific region moving along with a body movement of a subject by taking an image including said implanted marker inside one of said body of said subject and an image of said specific region of said subject from two different directions, the radiation fluoroscopy apparatus comprises:
  a radiation irradiation element;
    at least three different imaging systems each having a radiation detector that detects a radiation irradiated from said radiation irradiation element and transmitting said subject;
    an imaging system selection element that selects at least two of said at least three imaging systems, being used for a radiation fluoroscopy;
    said radiation fluoroscopy apparatus having at least said three imaging systems further comprises:
    a heat storage amount calculation circuit that calculates a respective heat storage amount of said radiation irradiation element, and
    wherein said imaging system selection element selects two of said imaging systems used for the radiation fluoroscopy based upon the heat storage amount of said radiation irradiation element calculated by said heat storage amount calculation circuit.

3. A radiation fluoroscopy apparatus, that detects a position of at least one of an implanted marker and a specific region moving along with a body movement of a subject by taking an image including at least one of said implanted marker inside the body of said subject and an image of said specific region of said subject from two different directions each other comprising:
  a radiation irradiation element;
  a first imaging system, a second imaging system, a third imaging system, and a fourth imaging system, each respectively having a radiation detector that detects a radiation irradiated from said radiation irradiation element and being transmitted to said subject;
  a first electric power supply circuit that supplies an electric power to said radiation irradiation element and said first imaging system and said second imaging system;
  a second electric power supply circuit supplies an electric power to said radiation irradiation element and said third imaging system and said fourth imaging system; and
  an imaging system selection circuit selects one of either said first imaging system and said second imaging system, and one of either said third imaging system and said fourth imaging system, as said imaging system used for a radiation fluoroscopy.

4. The radiation fluoroscopy apparatus, according to claim 3 comprising:
  a detection rate calculation circuit that calculates a respective detection rate of a position of one of said implanted markers and said specific regions relative to respective said first imaging system, said second imaging system, said third imaging system and said fourth imaging system; and
  wherein said imaging system selection circuit selects said imaging system having a higher detection rate of one of said implanted marker and said specific region calculated by said detection rate calculation circuit of either said first imaging system and said second imaging system, and also selects an imaging system having a higher detection rate of one of said implanted marker and said specific region, calculated by said detection rate calculation element of either of said third imaging system and said fourth imaging system.

5. The radiation fluoroscopy apparatus, according to claim 3, wherein:
  the radiation fluoroscopy apparatus further comprises:
  a heat storage amount calculation circuit that calculates the respective heat storages of the radiation irradiation element relative to the first imaging system, the second imaging system, the third imaging system, and the fourth imaging system; and
  wherein said imaging system selection element selects an imaging system having a lesser heat storage amount of said radiation irradiation element, calculated by said heat storage amount calculation circuit of either of said first imaging system and said second imaging system, and also selects an imaging system having a lesser heat storage amount of said radiation irradiation circuit, calculated by said heat storage amount calculation circuit of either of said third imaging system and said fourth imaging system.

* * * * *